United States Patent [19]
Sooknanan

[11] Patent Number: 6,025,134
[45] Date of Patent: Feb. 15, 2000

[54] USE OF RNA POLYMERASE TO IMPROVE NUCLEIC ACID AMPLIFICATION PROCESS

[75] Inventor: Roy Sooknanan, Toronto, Canada

[73] Assignee: Akzo Nobel N.V., Netherlands

[21] Appl. No.: 08/790,249

[22] Filed: Jan. 28, 1997

Related U.S. Application Data

[63] Continuation of application No. 08/275,250, Jul. 15, 1994, abandoned.

[51] Int. Cl.[7] .............................. C12Q 1/68; C12P 19/34
[52] U.S. Cl. ........................ 435/6; 435/91.2; 435/91.21
[58] Field of Search .......................... 435/6, 91.2, 91.21; 536/24.33

[56] References Cited

U.S. PATENT DOCUMENTS

| | | | |
|---|---|---|---|
| 5,130,238 | 7/1992 | Malek et al. | 435/91 |
| 5,409,818 | 4/1995 | Davey et al. | 435/91.21 |

FOREIGN PATENT DOCUMENTS

| | | |
|---|---|---|
| WO 91/01384 | 2/1991 | WIPO . |
| WO 91/02814 | 3/1991 | WIPO . |
| WO 91/02818 | 3/1991 | WIPO . |
| WO 91/04340 | 4/1991 | WIPO . |

OTHER PUBLICATIONS

Boom, R. et al. "Rapid and Simple Method for Purification of Nucleic Acids", 1990 *J Clin Micro.* 28:495–503.

Chamberlin, M.J. 1976. "RNA Polymerase" in Losick, R. and Chamberlin, M. (eds) in *Cold Spring Harbor Laboratory*, p. 17–67.

Ovchinnikov, Y.A. et al., 1977. "The Primary Structure of α–Subunit of DNA–Dependent RNA Polymerase from *Escherichia coli*", *FEBS Lett.* 76:108–111.

Sambrook, J. et al., 1989. "Molecular Cloning: a laboratory manual", 2nd ed. Cold Spring Harbor, NY: *CSH Laboratory Press*, p. 9.16–9.19 and p. 11.31–33.

Sooknanan, R. et al., 1993. "Detection and direct sequence identification of a BCR–ABL mRNA in Ph[+] chronic myeloid leukemia" *Experimental Hematology* 21:1719–1724.

Thrash et al., *J. Biolog. Chem.* 252(16), 5615–5618 (1977).

McClure et al., *J. Biol. Chem.* 253(24), 8949–8956 (1978).

Guatelli et al., *PNAS* 87, 1874–1878 (1990).

Kwoh et al., *PNAS* 86, 1173–1177 (1989).

Kievits et al., *J. Virol. Methods* 35, 273–286 (1991).

*Primary Examiner*—Kenneth R. Horlick
*Attorney, Agent, or Firm*—Burns, Doane, Swecker & Mathis, LLP

[57] ABSTRACT

This invention relates to the use of a eukaryotic or prokaryotic DNA-directed RNA polymerase of a class that synthesizes cellular RNA, in a process for the amplification of a specific nucleic acid sequence or of its complement. It also relates to a new process for amplifying a specific nucleic acid sequence. The process includes one or more reactions which may take place in a single reaction vessel. In one instance, in a first reaction, the process includes providing a first RNA polymerase which uses a DNA first template to synthesize an RNA first template, and, in a second reaction, providing the RNA first template and a number of other reagents such that the reagents use the RNA first template to synthesize a DNA second template and an RNA second template. Thereafter a cycle ensues in which the reagents use the RNA second template to synthesize a DNA third template and multiple copies of the RNA second template. The RNA second template is the specific nucleic acid sequence or its complement. This invention includes a kit containing the reagents of this invention.

53 Claims, 7 Drawing Sheets

I. Agarose gel

II. Northern blot

Ethidium bromide gel

Northern-blot

USE OF RNA POLYMERASE TO IMPROVE NUCLEIC ACID AMPLIFICATION PROCESS

This application is a continuation of application Ser. No. 08/275,250, filed Jul. 15, 1994 abandoned.

FIELD OF THE INVENTION

This invention relates to the use of DNA-directed RNA polymerase of a class that synthesizes cellular RNA to improve a process of amplifying a specific nucleic acid sequence.

BACKGROUND OF THE INVENTION

The presence of nucleic acids in a sample may indicate that a source from which the sample is taken has a disease, disorder or abnormal physical state. Certain diagnostics determine whether nucleic acids are present in a sample. These diagnostics invariably require amplification of nucleic acids because of the copy number problem. In a virus or cell, for example, there is usually a single copy of a particular gene. Without amplification of specific nucleic acids of the gene, it is often difficult to detect the presence of the nucleic acids.

There are a number of processes for amplifying nucleic acids. Two such processes are those described in U.S. Pat. No. 5,130,238 (Malek et al.) and U.S. Ser. No. 07/211,384 (Malek et al.), U.S. Pat. No. 5,409,818. Malek's amplification processes require less participation and fewer manipulations by the user. The amplification cycle takes place at a relatively constant ambient temperature and without the serial addition of reagents. The template nucleic acid sequence generates more than one product from one substrate in each cycle of the amplification process. The amplification processes use either DNA or RNA as a starting template.

Where single or double-stranded DNA is the starting template, Malek's processes require thermal or alkali denaturation before the amplification cycle.

Where single-stranded DNA is a starting template, a first primer hybridizes to the DNA. Then, a DNA-directed DNA polymerase makes a double-stranded DNA product. The product of the polymerization then undergoes either thermal or alkali denaturation before the single-stranded DNA enters the cycle.

Where double-stranded DNA is a starting template, the double-stranded DNA first undergoes either thermal or alkali denaturation. The first primer then hybridizes to one of the single strands of DNA. Then, a DNA-directed DNA polymerase makes a double-stranded DNA product. The product of the polymerization then undergoes a second thermal or alkali denaturation before the single-stranded DNA enters the cycle.

Thermal denaturation is problematic because entry into the amplification cycle is not isothermal. Alkali denaturation is problematic because it requires participation and manipulations by a user of the amplification process. Thermal denaturation may be used not only in Malek's processes, but in other amplification processes (for example, PCR and LCR).

Thus, a need exists for improvements to nucleic acid amplification to (1) decrease the number of steps involved in the process, (2) decrease the participation and manipulations by a user, (3) eliminate the heating steps involved in entering any amplification cycle, and (4) reduce the temperatures at which any heating takes place.

In this application, the phrase "specific nucleic acid sequence" means a sequence of single-stranded or double-stranded nucleic acids or a sequence complementary to such sequence which one wishes to amplify. "DNA-directed RNA polymerase" means such polymerase of a quality suitable for use in molecular biological reactions. One "unit" of a first RNA polymerase means the amount of RNA polymerase which catalyzes the incorporation of one nanomole of radio-labelled ribonucleoside triphosphate into an RNA first template in 10 minutes at 37° C.

SUMMARY OF THE INVENTION

This invention makes the amplification of nucleic acids more expedient, requiring less participation and fewer manipulations than conventional amplification processes. The amplification, including the entry into any amplification cycle, takes place at a relatively constant ambient temperature. The entry into the cycle does not require serial steps.

This invention relates to the use of a eukaryotic or prokaryotic DNA-directed RNA polymerase of a class that synthesizes cellular RNA, in a process for the amplification of a specific nucleic acid sequence. In one instance, the polymerase is *Escherichia coli* RNA polymerase. The use may also include the use of an inhibitor of such polymerase.

This invention also relates to a process for the amplification of a specific nucleic acid sequence. In one case, the process includes two steps (A)–(B).

Step (A)

In Step (A), one provides one or more reaction medium containing reagents including, a DNA first template; a first RNA polymerase which is a eukaryotic or prokaryotic RNA polymerase of a class that synthesizes cellular RNA; ribonucleoside triphosphates; deoxyribonucleoside triphosphates; a first oligonucleotide primer having a plus sequence of a promoter recognised by a second RNA polymerase; a second oligonucleotide primer; a second RNA polymerase which is a DNA-directed RNA polymerase that recognizes the promoter; an RNA-directed DNA polymerase; a DNA-directed DNA polymerase; a ribonuclease that hydrolyzes RNA of an RNA-DNA hybrid without hydrolyzing single or double-stranded RNA or DNA; and the RNA first template. The reagents may be combined in a variety of ways to provide one or more reaction mediums. A single reaction vessel may be used for the reactions.

In the process, (1) the first RNA polymerase uses the DNA first template to synthesize an RNA first template which includes the specific nucleic acid sequence or a sequence complementary to the specific nucleic acid sequence, (2) the first oligonucleotide primer hybridizes to the RNA first template, (3) the RNA-directed DNA polymerase uses the RNA first template to synthesize a DNA second template by extension of the first oligonucleotide primer and thereby forms an RNA-DNA hybrid intermediate, (4) the ribonuclease hydrolyzes RNA of the RNA-DNA hybrid intermediate, (5) the second oligonucleotide primer hybridizes to the DNA second template, (6) the DNA-directed DNA polymerase uses the second oligonucleotide primer and the DNA second template to synthesize a functional promoter recognized by the second RNA polymerase, and (7) the second RNA polymerase recognizes the functional promoter and transcribes the DNA second template, thereby providing the RNA second template.

Thereafter, a cycle ensues. In the cycle, (1) the second oligonucleotide primer hybridizes to the RNA second template, (2) the RNA-directed DNA polymerase uses the RNA second template to synthesize a DNA third template by extension of the second oligonucleotide primer and thereby forms an RNA-DNA hybrid intermediate, (3) the ribonuclease hydrolyzes RNA of the RNA-DNA hybrid intermediate, (4) the first oligonucleotide primer hybridizes to the DNA third template, (5) the DNA-directed DNA polymerase uses the first oligonucleotide primer as template to synthesize a functional promoter recognized by the second RNA polymerase by extension of the DNA third template, and (6) the second RNA polymerase recognizes the functional promoter and transcribes the DNA third template, thereby providing copies of the RNA second template.

Step (B)

In Step (B), one maintains the conditions for a time sufficient to achieve a desired amplification of the specific nucleic acid sequence or of a sequence complementary to the specific nucleic acid sequence.

In another case, the process includes three Steps (A)–(C). The process (all of Steps (A)–(C)) may take place in a single reaction vessel.

Step (A)

In Step (A), one provides a first reaction medium containing reagents including, (i) a DNA first template, (ii) a first RNA polymerase which is a eukaryotic or prokaryotic RNA polymerase, the polymerase being of a class that synthesizes cellular RNA, and (iii) ribonucleoside triphosphates. The RNA polymerase uses the DNA first template to synthesize an RNA first template which includes the specific nucleic acid sequence. The DNA first template could be double-stranded DNA or single-stranded DNA. The first RNA polymerase may be *Escherichia coli* RNA polymerase. The concentration of *Escherichia coli* RNA polymerase could be in the range of 1–3 units.

Step (B)

In Step (B), one provides a second reaction medium containing reagents including (i) a first oligonucleotide primer having a plus sequence of a promoter recognised by a second RNA polymerase, (ii) a second oligonucleotide primer, (iii) a second RNA polymerase which is a DNA-directed RNA polymerase that recognizes the promoter, (iv) an RNA-directed DNA polymerase, (v) a DNA-directed DNA polymerase, (vi) a ribonuclease that hydrolyzes RNA of an RNA-DNA hybrid without hydrolyzing single or double-stranded RNA or DNA, (vii) ribonucleoside and deoxyribonucleoside triphosphates, and (viii) the RNA first template, under conditions such that (1) the first oligonucleotide primer hybridizes to the RNA first template, (2) the RNA-directed DNA polymerase uses the RNA first template to synthesize a DNA second template by extension of the first oligonucleotide primer and thereby forms an RNA-DNA hybrid intermediate, (3) the ribonuclease hydrolyzes RNA of the RNA-DNA hybrid intermediate, (4) the second oligonucleotide primer hybridizes to the DNA second template, (5) the DNA-directed DNA polymerase uses the second oligonucleotide primer and the DNA second template to synthesize a functional promoter recognized by the second RNA polymerase, and (6) the second RNA polymerase recognizes the functional promoter and transcribes the DNA second template, thereby providing an RNA second template.

Thereafter, a cycle ensues. In the cycle, (1) the second oligonucleotide primer hybridizes to the RNA second template, (2) the RNA-directed DNA polymerase uses the RNA second template to synthesize a DNA third template by extension of the second oligonucleotide primer and thereby forms an RNA-DNA hybrid intermediate, (3) the ribonuclease hydrolyzes RNA of the RNA-DNA hybrid intermediate, (4) the first oligonucleotide primer hybridizes to the DNA third template, (5) the DNA-directed DNA polymerase uses the first oligonucleotide primer as template to synthesize a functional promoter recognized by the second RNA polymerase by extension of the DNA third template, and (6) the second RNA polymerase recognizes the functional promoter and transcribes the DNA third template, thereby providing copies of an RNA second template.

Step (C)

Thereafter, in Step (C), one maintains the conditions for a time sufficient to achieve a desired amplification of the specific nucleic acid sequence or of a sequence complementary to the specific nucleic acid sequence. For example, one may maintain the conditions for a time between 30 minutes and 4 hours.

In Step (A), the first reaction medium could also include deoxyribonucleoside triphosphates. In such a situation, the deoxyribonucleoside triphosphates and the ribonucleoside triphosphates need not be added to the second reaction medium.

In Step (B), the second reaction medium may also include an inhibitor of the first RNA polymerase. In one case, the inhibitor is rifampicin which is provided at a concentration in the range of 10–100 μg per ml. In the alternative, rather than using an inhibitor of the first RNA polymerase, Step (A) could be followed by heating the first reaction medium before Step (B). The first reaction medium would be heated to about 65° C.

In Step (B), the second reaction medium could include an alkylated sulfoxide and a suitable carrier protein. The alkyl sulfoxide may be dimethylsulfoxide (DMSO) and the carrier protein may be bovine serum albumin (BSA).

The first oligonucleotide primer may also include a plus sequence of a transcription initiation site for the second RNA polymerase. The plus sequence of the transcription initiation site would be operatively linked to the plus sequence of the promoter. The second RNA polymerase could be bacteriophage T7 RNA polymerase. In such a case, the plus sequence of the transcription initiation site and the plus sequence of the promoter together are the nucleotide sequence SEQ ID NO: 1:

5'-AATTCTAATACGACTCACTATAGGGAGA-3'

After Step (C), the process may include a Step (D) of monitoring the reaction medium for consumption of any of the reagents (i), (ii) and (vii) of Step (B) or for accumulation of any product of the cycle. Step (D) could be (1) detecting a nucleic acid product of the cycle using a nucleic acid probe, or restriction endonucleases and electrophoretic separation, (2) monitoring the accumulation of the RNA second template, (3) monitoring the accumulation of the DNA second template, (4) monitoring DNA containing a functional promoter recognized by the RNA polymerase, (5) monitoring the accumulation of the RNA-DNA hybrid intermediate, (6) monitoring consumption of any reagent of the reagents (i), (ii) and (vii) of Step (B) or accumulation of any product of the cycle with a value representing consumption of the reagent or accumulation of the product in the second reaction medium in the absence of the specific nucleic acid sequence.

In the process, the ribonuclease could be *Escherichia coli* ribonuclease H or calf thymus ribonuclease H. The first oligonucleotide primer or the second oligonucleotide primer could be bound reversibly to an immobilized support. The DNA-directed RNA polymerase could be bacteriophage RNA polymerase, bacteriophage T7 RNA polymerase, bacteriophage T3 polymerase, bacteriophage ΦII polymerase, Salmonella bacteriophage sp6 polymerase, or Pseudomonas bacteriophage gh-1 polymerase. The RNA-directed DNA polymerase could be retrovirus reverse transcriptase such as an avian myeloblastosis virus polymerase or a Moloney murine leukemia virus polymerase.

In one instance, the DNA-directed DNA polymerase lacks DNA exonuclease activity. In another instance, all DNA polymerases in the second reaction medium lack DNA exonuclease and DNA endonuclease activity. The DNA-directed DNA polymerase could be avian myeloblastosis virus polymerase, DNA polymerase a or DNA polymerase β, or calf thymus DNA polymerase.

The process may include the steps of ligating a DNA product of the cycle into a cloning vector and then cloning the DNA product, expressing a product encoded by the DNA product of the cycle in an expression system.

The invention includes a kit for amplifying nucleic acid sequences. The kit includes one or more receptacles containing (a) a first RNA polymerase which is a DNA-directed RNA polymerase which synthesizes cellular RNA, (b) ribonucleoside triphosphates, (c) deoxyribonucleoside triphosphates, (d) a first oligonucleotide primer including a plus sequence of a promoter recognized by a second RNA polymerase, (e) a second oligonucleotide primer, (f) a second RNA polymerase which is a DNA-directed RNA polymerase that recognizes the promoter, (g) an RNA-directed DNA polymerase, (h) a DNA-directed DNA polymerase, and (i) a ribonuclease that hydrolyzes RNA of an RNA-DNA hybrid without hydrolyzing single- or double-stranded RNA or DNA.

In the kit, the first RNA polymerase may be Escherichia coli RNA polymerase. The kit may also include an inhibitor of Escherichia coli RNA polymerase. In one instance, the inhibitor is rifampicin.

The kit may also include an alkylated sulfoxide and a suitable carrier protein.

BRIEF DESCRIPTION OF THE DRAWINGS

In drawings which illustrate embodiments of the invention,

FIG. 4A shows the results of an agarose gel containing ethidium bromide and FIG. 4B shows a northern blot hybridization.

DETAILED DESCRIPTION OF THE PREFERRED EMBODIMENTS

Figure 1:
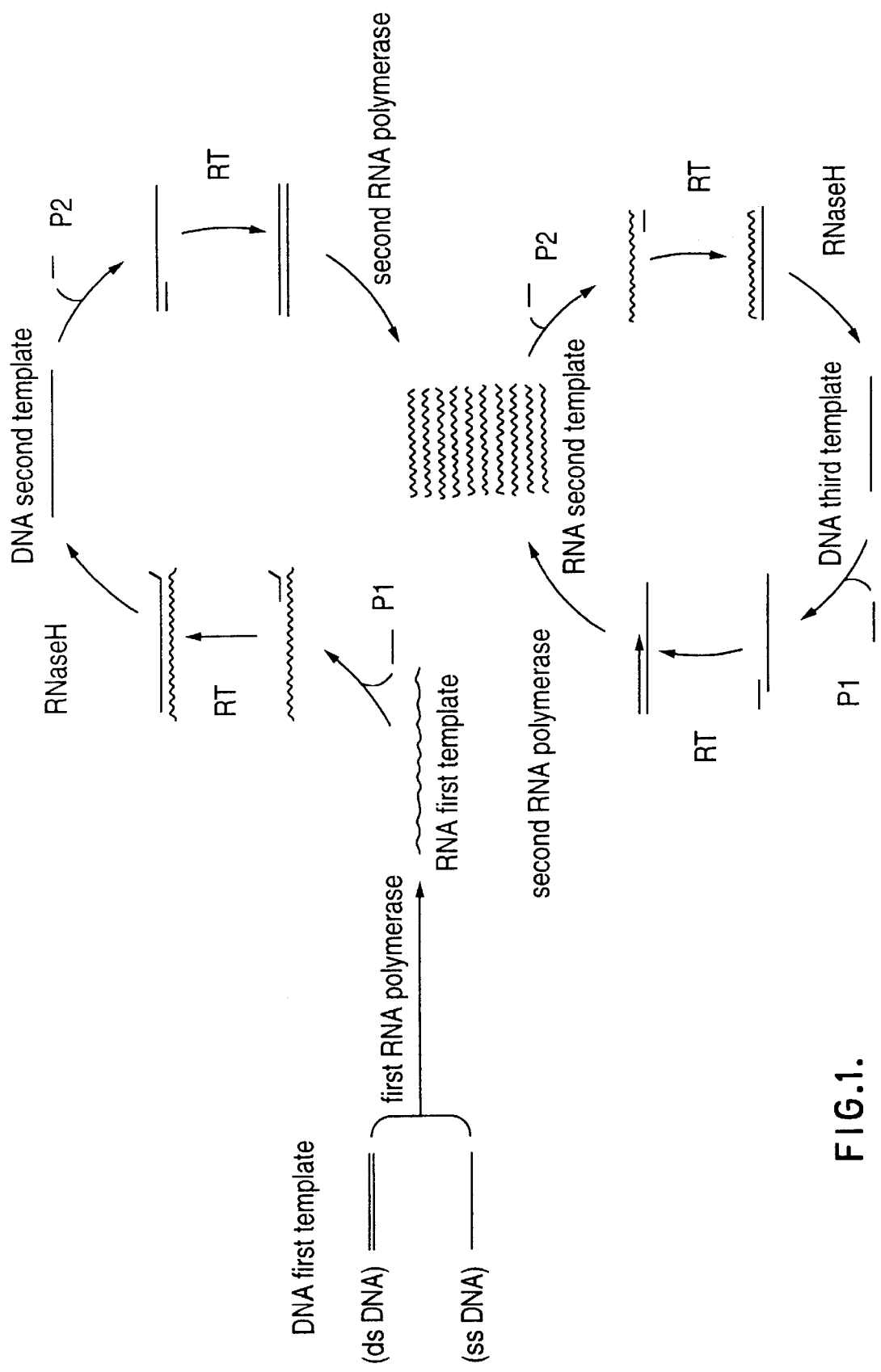
FIG. 1 is a general illustration of a nucleic acid amplification process starting with double-stranded DNA or with single-stranded DNA.

This invention relates to the use of a eukaryotic or prokaryotic DNA-directed RNA polymerase which is of a class that synthesizes cellular RNA, in a process for the amplification of a specific nucleic acid sequence. In one embodiment, such polymerase is used in the amplification process which is described in U.S. Ser. No. 07/211,384 (Malek et al), U.S. Pat. No. 5,409,818. In another embodiment, such polymerase is used in the amplification process which is described in U.S. Pat. No. 5,130,238 (Malek et al.). In such embodiments, this invention relates to a novel process for entering the amplification cycle.

To a first reaction medium containing single-stranded or double-stranded DNA (DNA first template) suspected of containing or known to contain a specific nucleic acid sequence, one adds Escherichia coli RNA polymerase and ribonucleoside triphosphates. The Escherichia coli RNA polymerase non-specifically transcribes the DNA template independent of specific promoter sequences (Chamberlin, 1976; Ovchinnikov et al., 1977) to provide an RNA first template. One can use either Escherichia coli RNA polymerase holo or core enzyme, however, the core is preferred because of the increased promoter independent transcription due to the absence of the sigma factor.

Following transcription of the DNA first template, there is at least one RNA copy (an RNA first template) for each DNA first template. After obtaining the RNA first template, one provides a second reaction medium. A description of the reagents used in the second reaction medium is provided in the Summary of the Invention.

In the second reaction medium, the first primer hybridizes to the RNA first template, the RNA-directed DNA polymerase uses the RNA first template to synthesize a DNA second template by extending the first primer, resulting in a RNA-DNA hybrid intermediate. The ribonuclease hydrolyzes RNA of the RNA-DNA hybrid. The second primer hybridizes to the DNA second template. The DNA-directed DNA polymerase uses the second primer and the DNA second template to synthesize a functional promoter recognized by the second RNA polymerase. The second RNA polymerase recognizes the functional promoter and transcribes the DNA second template providing copies of the RNA second template. The RNA second template then enters the cycle described in U.S. Pat. No. 5,130,238 and in U.S. Ser. No. 07/211,384 (Malek et al.) such that the process results in multiple copies of the specific nucleic acid sequence.

Thus, this improvement eliminates the need for DNA strand separation and first primer-primed extension of the DNA first template. The DNA first template is used in a single transcription reaction rather than in a separate priming reaction before amplification of a specific nucleic acid.

MATERIALS AND METHODS

Materials

Oligonucleotides were synthesized using an Applied Biosystems DNA synthesizer. Columns, phosphoramidites, and reagents used for oligonucleotide synthesis were purchased from Applied Biosystems, Inc. Oligonucleotides were purified by polyacrylamide gel electrophoresis followed by DEAE cellulose chromatography. The radioisotope $\alpha\text{-}^{32}P$-CTP (~3000 Cl/mmol) and $\gamma\text{-}^{32}P$-ATP (~3000 Cl/mmol) (was from Amersham. RNase A and rifampicin were purchased from Sigma. DNase I was obtained from Promega.

*Escherichia coli* RNA polymerase was purchased from Boehringer Mannheim and Epicentre Technologies Inc.

Isolation of DNA and sequencing

The purification of genomic DNA from KG-1 and *Salmonella typhimurium* cells was according to Sambrook et al., 1989. Total nucleic acids were isolated from Chlamydia infected HeLa cells according to Boom et al., 1990.

Agarose Gel Electrophoresis and Northern Blot Hybridization

Agarose gels were prepared and run according to Sambrook et al., 1989. The gels contained either 3% low-melt agarose (NuSieve™; FMC) and 1% agarose or only 2% agarose in 1× Tris-acetate EDTA (TAE) with 0.2 µg/ml ethidium bromide. Aliquots (5 µl) of the amplification reactions were analysed.

Following electrophoresis, the amplified materials were transferred to a nylon membrane by electroblotting (Sambrook et al., 1989). The nucleic acids were fixed to the nylon membrane and hybridized to specific probes using conditions described by Sooknanan et al., 1993. The probes were labelled at the 5'-end with $^{32}$P (Sambrook et al., 1989). Following hybridization and the removal of non-specifically bound probe by washing, autoradiography was performed using Kodak XAR-5 film.

TCA Precipitation

Aliquots (5 µl) of transcription reactions were TCA precipitated according to Sambrook et al., 1989. Radioactivity was determined in a liquid scintillation counter.

EXAMPLE 1

Transcription of Native Genomic DNA in vitro using *Escherichia coli* RNA Polymerase A standard *Escherichia coli* RNA polymerase transcription reaction comprised 66.67 mM Tris (pH 8.5), 83.3 mM KCl, 20 mM MgCl$_2$, 3.3 mM of each ATP, CTP, GTP and UTP, 1.6 mM of each dATP, dCTP, dGTP and dTTP, 5 µg bovine serum albumin, 16.6 mM DTT, 7.5 units placental ribonuclease inhibitor, ≦500 ng double-stranded DNA and 1 unit *Escherichia coli* RNA polymerase core enzyme in a final volume of 15 µl. The reaction mixture was incubated at 40° C. for 30 minutes.

Figure 2:
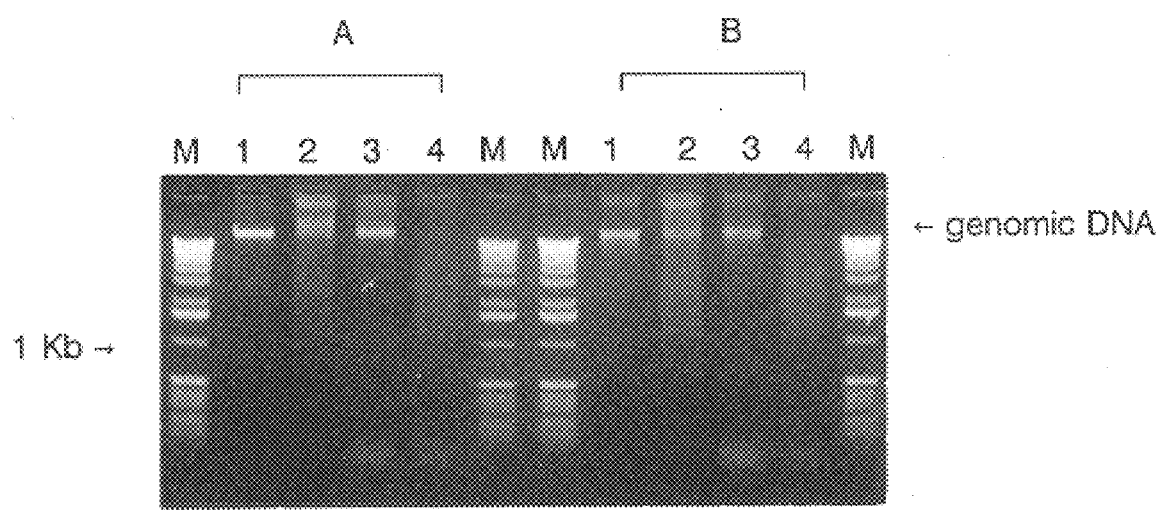
FIG. 2 shows the sensitivity of transcripts generated by using Escherichia coli RNA polymerase and genomic DNA to RNase A and DNase I.

In order to demonstrate transcription of the DNA template by *Escherichia coli* RNA polymerase, aliquots of the transcription reactions were digested with either 2 µg RNase A (RNA specific nuclease) or 2 units DNase I (DNA specific nuclease) at 37° C. for 30 minutes and then analyzed on an ethidium bromide stained agarose gel. FIG. 2, lanes A2 and B2 show the transcription products from 100 ng of native DNA isolated from human myeloid cell line KG-1 and *Salmonella typhimurium*, respectively. The transcription products were sensitive to RNase A (FIG. 2, lanes A3 and B3) but not to DNase I (FIG. 2, lanes A4 and B4) confirming that the synthesized product was RNA. DNase I digested the input DNA template as expected (FIG. 2, lanes A4 and B4). In addition, the majority of the RNA synthesized appeared to be a heterogenous mixture as indicated by the smear extending above the 1 Kb DNA molecular weight marker on the native ethidium bromide stained agarose gel.

In FIG. 2, the following lanes have the following materials:

A—250 ng KG-1 genomic DNA
B—250 ng Salmonella typhimurium genomic DNA
M—double-strand DNA molecular weight marker
1—mock transcription reaction (no enzyme)
2—untreated transcription reaction
3—RNase A treated transcription reaction
4—DNase I treated transcription reaction

EXAMPLE 2

Specific Inhibition of *Escherichia coli* RNA Polymerase without Inhibiting NASBA™

Figure 3A:
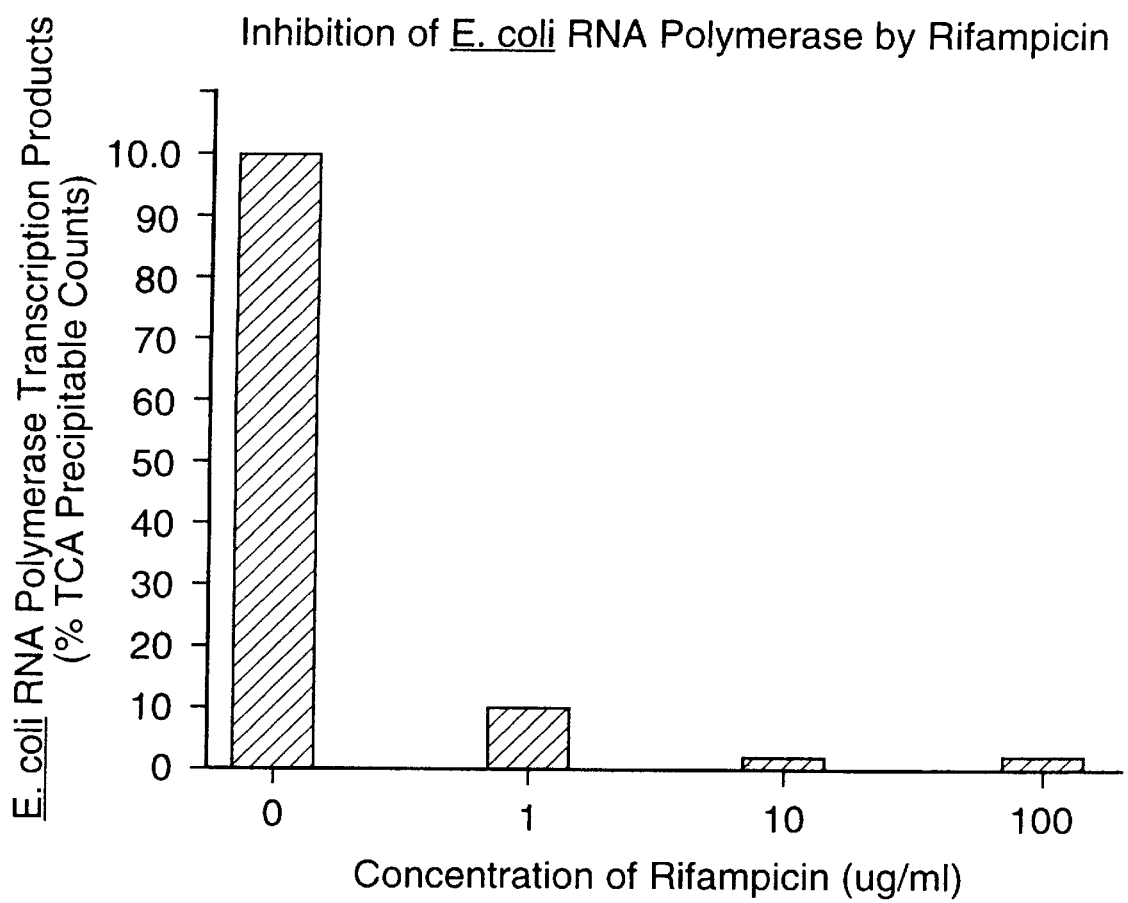
FIG. 3A shows the inhibition of Escherichia coli RNA polymerase by rifampicin.

*Escherichia coli* RNA polymerase must be inactivated following transcription to prevent the inhibition of NASBA™. *Escherichia coli* RNA polymerase reactions containing 1.7 pmoles α-$^{32}$P-CTP, 100 ng native genomic DNA and 0, 1, 10 or 100 µg/ml rifampicin were performed as described in FIG. 3A.

The levels of RNA synthesized were measured by TCA precipitation of the transcribed materials. Both 10 and 100 µg/ml rifampicin were sufficient to inhibit 1 unit of *Escherichia coli* RNA polymerase resulting in less than 2% RNA synthesis compared to 10% for 1 mg/ml rifampicin and 100% when no rifampicin was present (FIG. 3A).

Figure 3B:
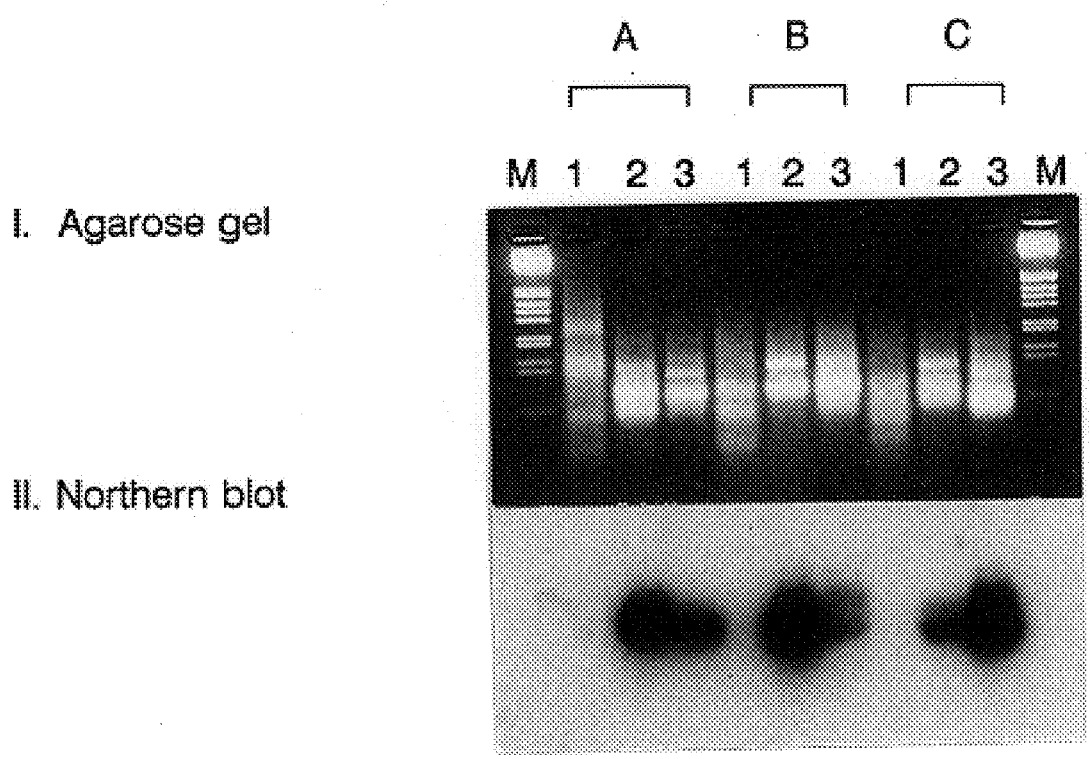
FIG. 3B shows the effect of rifampicin in NASBA™ amplification. I shows an agarose gel containing ethidium bromide. II shows a northern blot hybridization.

On the other hand, rifampicin at either 10 µg/ml or 100 µg/ml concentrations did not appear to inhibit NASBA™ reactions compared to no added rifampicin (FIG. 3B). It was also possible to inactivate *Escherichia coli* RNA polymerase by incubating the transcription reactions at 65° C. for at least 2 minutes (data not shown).

In FIG. 3B, I shows an agarose gel containing ethidium bromide, II shows a northern blot hybridization.

In FIG. 3B, the following lanes have the following materials:

A—no rifampicin
B—10 µg/ml rifampicin
C—100 µg/ml rifampicin
M—double-strand DNA molecular weight marker
1—no added template
2,3—10 ng P1-primed genomic DNA as template

EXAMPLE 3

Evidence for Specific Amplification from RNA Transcribed by *Escherichia coli* RNA Polymerase from Double-strand DNA Template Six separate transcription reactions each containing 10 ng of native human genomic DNA were performed as shown in FIG. 2. The reactions were pooled and redivided into 6 equal amounts for the purpose of standardization. Two of the aliquots were then digested with 2 µg RNase A each and another two with 2 units DNase I each as described in FIG. 2. The final two aliquots were incubated as the others but without any added nuclease.

Following the incubation, the samples were deproteinized and the nucleic acids recovered after ethanol precipitation in 5 µl of sterile H$_2$O. Each 5 µl sample was then added to standard NASBA™ reactions containing GM-CSF specific primers and allowed to amplify for 90 minutes at 40° C. In parallel, duplicate NASBA™ reactions each containing 10 ng of untreated native HGD were also performed.

Figure 4A:
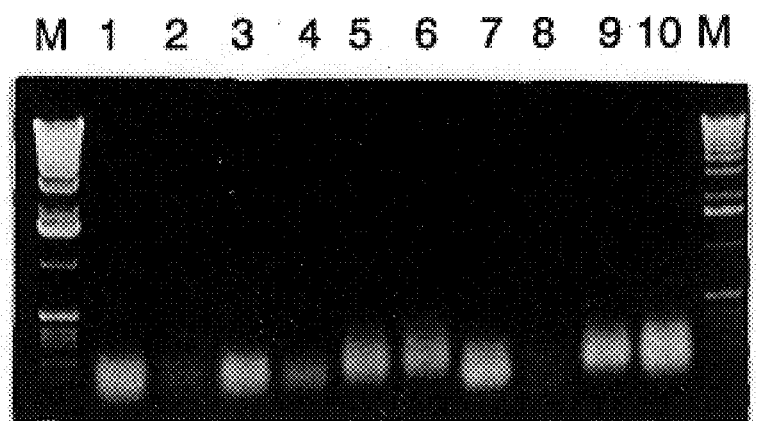
FIGS. 4A and 4B show the evidence for specific amplification from transcriptions generated from Escherichia coli RNA polymerase where
Figure 4B:
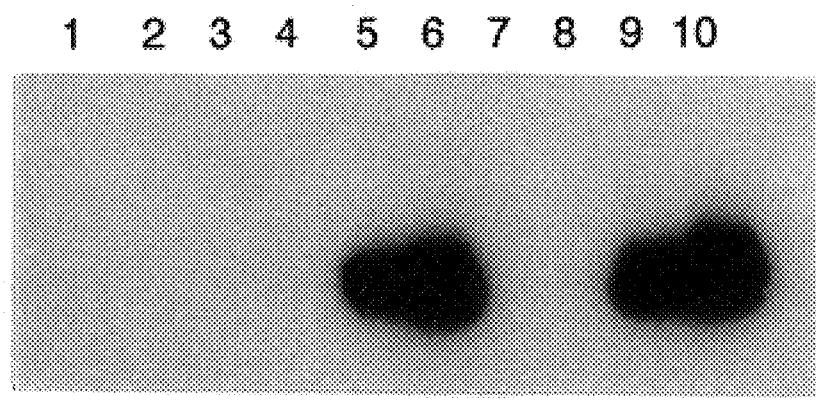

The products contained in 5 µl aliquots of the amplification reactions were analyzed on an ethidium bromide stained agarose gel followed by Northern blot hybridization. All of the reactions contained amplified materials based on ethidium bromide staining (FIG. 4a, lanes 1–10) indicating that the amplification reactions were not inhibited. However, after hybridization with a probe specific for the amplified GM-CSF sequence, positive signals were seen only from reactions containing the undigested transcribed material (FIG. 4b, lanes 5, 6) and the DNase I digested material (FIG. 4b, lanes 9, 10). The reactions containing either the native DNA or the RNase A digested material were negative (FIG. 4b, lanes 2, 3 and 7, 8 respectively). These results indicated that the GM-CSF specific amplification originated from RNA generated after transcription of native DNA by *Escherichia coli* RNA polymerase.

In FIG. 4b, the following lanes have the following materials:

1—no added template 2,3—10 ng native DNA as template

4—no added template 5,6—untreated transcription reaction as template 7,8—RNase A treated transcription reaction as template 9,10—DNase I treated transcription reaction as template

EXAMPLE 4
Amplification in NASBA™ of Specific Sequences from RNA Generated after *Escherichia coli* RNA Polymerase Transcription of Human Genomic DNA (HGD)

*Escherichia coli* RNA polymerase transcription reactions containing 1 ng, 10 ng or 100 ng of HGD were performed as described in FIG. 2. Following transcription, the appropriate primer mixture was added directly to the transcription reaction to give a final concentration in a 25 µl volume of 0.2 µM of the first primer (P1), 0.2 µM of the second primer (P2) and 15% (v/v) DMSO. The reaction mixture was heated at 65° C. for 2 minutes and then transferred to 40° C. After 2 minutes at 40° C., an enzyme mixture containing 8 units AMV reverse transcriptase, 0.2 units RNase H, 40 units T7 RNA polymerase and 100 µg/ml BSA was added to each reaction and the final reaction volume adjusted to 25 ml with $H_2O$. The reactions were incubated at 40° C. for an additional 90 minutes.

In parallel, 1 ng, 10 ng and 100 ng of HGD were denatured and P1 primed. The P1-primed DNA was separated by thermal denaturation and added to standard 25 µl NASBA™ reactions (40 mM Tris, pH 8.5, 50 mM KCl, 12 mM $MgCl_2$, 2 mM of each ATP, CTP, GTP and UTP, 1 mM of each dATP, dCTP, dGTP and dTTP, 10 mM DTT, 8 units AMV reverse transcriptase, 0.2 units RNase H, 40 units T7 RNA polymerase and 100 µg/ml BSA) and incubated at 40° C. for 90 minutes. A third set of standard NASBA™ reactions containing 1 ng, 10 ng or 100 ng of untreated native HGD as templates were also performed.

Figure 5:
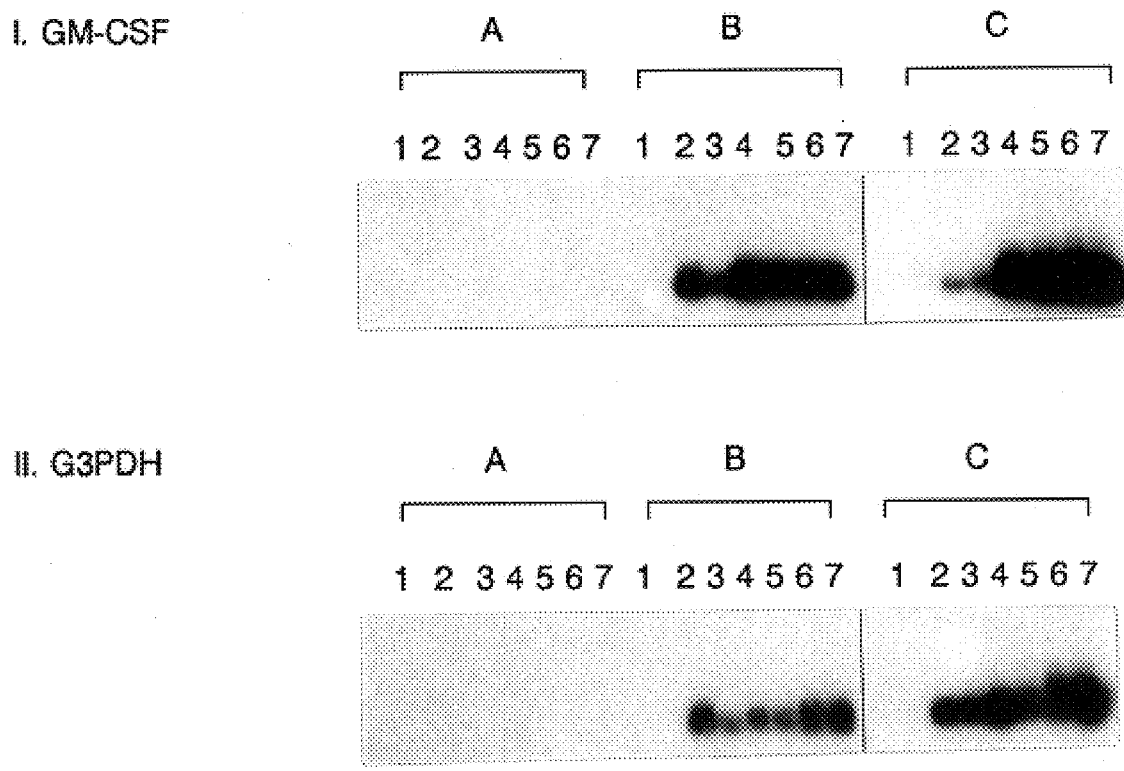
FIG. 5 shows the specific amplification of (I) GM-CSF and (II) G3PDH Sequences from transcripts generated using Escherichia coli RNA polymerase.

Following amplification, a 5 µl aliquot of each reaction was analyzed on an ethidium bromide stained agarose gel followed by Northern blot hybridization. The results for primers specific for GM-CSF and G3PDH sequences are shown in FIG. 5 I and 5 II respectively. The ability to amplify specific DNA sequences from the RNA generated after transcription of the DNA with *Escherichia coli* RNA polymerase was the same when compared to the conventional P1-priming procedure (FIGS. 5 I and II, lanes C2–7 and B2–7 respectively). The untreated DNA gave no specific amplification for either primer set (FIG. 5 I and II, lanes A2–7).

In FIG. 5, the following lanes have the following materials:

A—untreated native DNA

B—P1-primed DNA

C—*Escherichia coli* RNA polymerase RNA from DNA

1—no template 2,3—100 pg DNA 4,5—1 ng DNA 6,7—10 ng DNA

EXAMPLE 5
Amplification in NASBA™ of Specific Sequences from RNA Generated after *Escherichia coli* RNA Polymerase Transcription of *Chlamydia trachomatis* DNA; a Bacterial Model

*Escherichia coli* RNA polymerase transcription reactions containing different amounts of total nucleic acids isolated from *Chlamydia trachomatis* infected HeLa cells were performed as described in FIG. 2. Primers specific for the cryptic plasmid (PL1) and the MOMP gene (VD1) of *Chlamydia trachomatis* were tested in NASBA™. Following transcription, the appropriate primer mixture was added directly to the transcription reaction to give a final concentration in a 25 µl volume of 0.2 µM P1, 0.2 µM P2 and 15% (v/v) DMSO. The reactions were heated at 65° C. for 2 minutes and then transferred to 40° C. After 2 minutes at 40° C., a NASBA™ enzyme mixture containing 8 units AMV reverse transcriptase, 0.2 unit RNase H, 40 units T7 RNA polymerase and 100 µg/ml BSA was added to each reaction. The final reaction volume was adjusted to 25 ml with $H_2O$ and the reactions were incubated at 40° C. for an additional 90 minutes. Parallel NASBA™ reactions were performed with P1-primed material and neat material at similar concentrations.

Following amplification, a 5 µl aliquot of each reaction was analyzed by Northern blot hybridization. Specific amplification from PL1 and VD1 primers was observed from 10 pg and 1 pg of untreated total nucleic acids (neat) respectively (FIG. 6 I, lanes A6–7 and FIG. 6 II, lanes A6–7) likely due to RNA already contained in the sample. However, after transcription with *Escherichia coli* RNA polymerase, specific amplification for both PL1 and VD1 primers was obtained from 100 fg of total nucleic acids (FIG. 6 I, lanes C2–3 and FIG. 6 II, lanes C4–5) which was similar to the amplification when the P1-priming procedure for DNA was used (FIG. 6 I, lanes B2–3 and FIG. 6 II, lanes B4–5).

Figure 6:
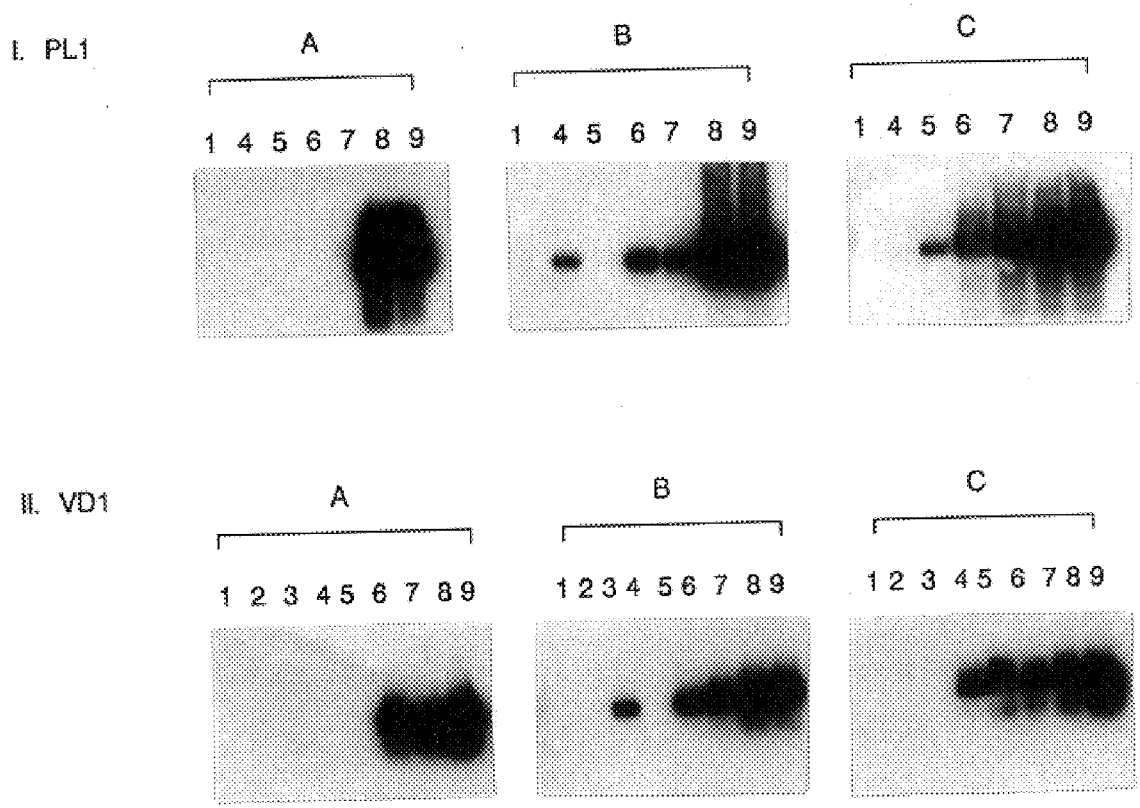
FIG. 6 shows the amplification in NASBA™ of specific sequences of Chlamydia trachomatis from Escherichia coli RNA polymerase generated RNA, (I) PL1, and (II) VD1.

In FIG. 6, the following lanes have the following material:

A—untreated total nucleic acids

B—P1-primed DNA

C—*Escherichia coli* RNA polymerase RNA from DNA

1—no template 2,3—10 fg total nucleic acids 4,5—100 fg total nucleic acids 6,7—1 pg total nucleic acids 8,9—10 pg total nucleic acids Although preferred embodiments of the invention have been described in detail, it will be understood by those skilled in the art that variations may be made to the invention without departing from either the spirit of the invention or the scope of the appended claims.

REFERENCES

1. Boom, R. et al. 1990. J. Clin. Micro. 28: 495
2. Chamberlin, M. J., 1976. RNA polymerase Losick, R and Chamberlin, M., (eds). Cold Spring Harbor Laboratory
3. Ouchinnikov, Y. A. et al., 1977. FEBS Lett. 76: 108
4. Sambrook, J. et al., 1989. Molecular cloning: a laboratory manual, 2nd ed. Cold Spring Harbor, N.Y.: CSH Laboratory Press.
5. Sooknanan, R. et al., 1993. Experimental Hematology 21: 1719.

I claim:

1. A process for the amplification of a specific DNA sequence in a sample, comprising a) providing in one reaction vessel reagents comprising
  (i) a first DNA-directed RNA polymerase wherein said polymerase is capable of non-specifically transcribing a double-stranded DNA template independent of specific promoter sequences;
  (ii) a double-stranded DNA first template comprising the specific DNA sequence;
  (iii) ribonucleoside triphosphates;
  (iv) deoxyribonucleotide triphosphates;
  (v) a first oligonucleotide primer comprising a plus sequence of a promoter recognized by a second RNA polymerase;
  (vi) a second oligonucleotide primer;
  (vii) a second RNA polymerase which is a DNA-directed RNA polymerase that recognizes said promoter;
  (viii) an RNA-directed DNA polymerase;
  (ix) a DNA-directed DNA polymerase;
  (x) a ribonuclease that hydrolyzes RNA of an RNA-DNA hybrid without hydrolyzing single or double-stranded RNA or DNA; and under conditions such that,
  (1) said first RNA polymerase uses said DNA first template to synthesize an RNA first template which comprises an RNA sequence which corresponds to said specific DNA sequence or a sequence complementary to said specific DNA sequence,
  (2) said first oligonucleotide primer hybridizes to said RNA first template,
  (3) said RNA-directed DNA polymerase uses said RNA first template to synthesize a DNA second template by extension of said first oligonucleotide primer and thereby forms an RNA-DNA hybrid intermediate,
  (4) said ribonuclease hydrolyzes RNA which comprises said RNA-DNA hybrid intermediate,
  (5) said second oligonucleotide primer hybridizes to said DNA second template,
  (6) said DNA-directed DNA polymerase uses said second oligonucleotide primer and said DNA second template to synthesize a functional promoter recognized by said second RNA polymerase, and
  (7) said second RNA polymerase recognizes said functional promoter and transcribes said DNA second template, thereby providing copies of an RNA second template; and b) maintaining the conditions for a time sufficient such that a cycle ensues to achieve amplification of the specific DNA sequence.

2. A process for the amplification of a specific DNA sequence in a sample, comprising a) providing in one reaction vessel reagents comprising
  (i) a first DNA-directed RNA polymerase wherein said polymerase is capable of non-specifically transcribing a DNA template independent of specific promoter sequences;
  (ii) a DNA first template comprising the specific DNA sequence;
  (iii) ribonucleoside triphosphates;
  (iv) deoxyribonucleotide triphosphates;
  (v) a first oligonucleotide primer comprising a plus sequence of a promoter recognized by a second RNA polymerase;
  (vi) a second oligonucleotide primer;
  (vii) a second RNA polymerase which is a DNA-directed RNA polymerase that recognizes said promoter;
  (viii) an RNA-directed DNA polymerase;
  (ix) a DNA-directed DNA polymerase;
  (x) a ribonuclease that hydrolyzes RNA of an RNA-DNA hybrid without hydrolyzing single or double-stranded RNA or DNA; and
  (xi) an inhibitor of the polymerase capable of non-specifically transcribing a DNA template independent of specific promoter sequences under conditions such that,
  (1) said first RNA polymerase uses said DNA first template to synthesize an RNA first template which comprises an RNA sequence which corresponds to said specific DNA sequence or a sequence complementary to said specific DNA sequence,
  (2) said first oligonucleotide primer hybridizes to said RNA first template.
  (3) said RNA-directed DNA polymerase uses said RNA first template to synthesize a DNA second template by extension of said first oligonucleotide primer and thereby forms an RNA-DNA hybrid intermediate.

(4) said ribonuclease hydrolyzes RNA which comprises said RNA-DNA hybrid intermediate,
(5) said second oligonucleotide primer hybridizes to said DNA second template,
(6) said DNA-directed DNA polymerase uses said second oligonucleotide prime and said DNA second template to synthesize a functional promoter recognized by said second RNA polymerase, and
(7) said second RNA polymerase recognizes said functional promoter and transcribes said DNA second template, thereby providing copies of an RNA second template; and b) maintaining the conditions for a time sufficient such that a cycle ensues to achieve amplification of the specific DNA sequence.

3. A process for the amplification of a specific nucleic acid sequence, comprising the steps of:
  (A) providing in one reaction vessel reagents comprising,
    (i) a double-stranded DNA first template comprising the specific nucleic acid sequence,
    (ii) a first RNA polymerase which is capable of non-specifically transcribing a double-stranded DNA template independent of specific promoter sequences,
    (iii) ribonucleoside triphosphates;
    (iv) deoxyribonucleotide triphosphates,
    (v) a first oligonucleotide primer, comprising a plus sequence of a promoter recognized by a second RNA polymerase,
    (vi) a second oligonucleotide primer,
    (vii) a second RNA polymerase which is a DNA-directed RNA polymerase that recognizes said promoter,
    (viii) an RNA-directed DNA polymerase,
    (ix) a DNA-directed DNA polymerase, and
    (x) a ribonuclease that hydrolyzes RNA of an RNA-DNA hybrid without hydrolyzing single or double-stranded RNA or DNA,
  under conditions such that,
    (1) said first RNA polymerase uses said DNA first template to synthesize an RNA first template which comprises said specific nucleic acid sequence or a sequence complementary to said specific nucleic acid sequence,
    (2) said first oligonucleotide primer hybridizes to said RNA first template,
    (3) said RNA-directed DNA polymerase uses said RNA first template to synthesize a DNA second template by extension of said first oligonucleotide primer and thereby forms an RNA-DNA hybrid intermediate,
    (4) said ribonuclease hydrolyzes RNA which comprises said RNA-DNA hybrid intermediate,
    (5) said second oligonucleotide primer hybridizes to said DNA second template,
    (6) said DNA-directed DNA polymerase uses said second oligonucleotide primer and said DNA second template to synthesize a functional promoter recognized by said second RNA polymerase, and
    (7) said second RNA polymerase recognizes said functional promoter and transcribes said DNA second template, thereby providing copies of an RNA second template,
  and thereafter a cycle ensues wherein
    (1) said second oligonucleotide primer hybridizes to said RNA second template,
    (2) said RNA-directed DNA polymerase uses said RNA second template to synthesize a DNA third template by extension of said second oligonucleotide primer and thereby forms an RNA-DNA hybrid intermediate,
    (3) said ribonuclease hydrolyzes RNA of said RNA-DNA hybrid intermediate,
    (4) said first oligonucleotide primer hybridizes to said DNA third template,
    (5) said DNA-directed DNA polymerase uses said first oligonucleotide primer as template to synthesize a functional promoter recognized by said second RNA polymerase by extension of said DNA third template, and
    (6) said second RNA polymerase recognizes said functional promoter and transcribes said DNA third template, thereby providing copies of said RNA second template,
  and thereafter
  (B) maintaining said conditions for a time sufficient to achieve a desired amplification of said specific nucleic acid sequence or of a sequence complementary to said specific nucleic acid sequence.

4. A process for the amplification of a specific nucleic acid sequence, comprising the steps of:
  (A) providing reagents comprising at least,
    (i) a double-stranded DNA first template comprising the specific nucleic acid sequence,
    (ii) a first RNA polymerase which is capable of non-specifically transcribing a double-stranded DNA template independent of specific promoter sequences,
    (iii) ribonucleoside triphosphates;
  under conditions such that such first RNA polymerase uses said DNA first template to synthesize an RNA first template which comprises said specific nucleic acid sequence or a sequence complementary to said specific nucleic acid sequence,
  (B) providing in one or more steps reagents comprising,
    (i) a first oligonucleotide primer, comprising a plus sequence of a promoter recognized by a second RNA polymerase,
    (ii) a second oligonucleotide primer,
    (iii) a second RNA polymerase which is a DNA-directed RNA polymerase that recognizes said promoter,
    (iv) an RNA-directed DNA polymerase,
    (v) a DNA-directed DNA polymerase,
    (vi) a ribonuclease that hydrolyzes RNA of an RNA-DNA hybrid without hydrolyzing single or double-stranded RNA or DNA, and
    (vii) ribonucleoside and deoxyribonucleotide triphosphates,
  under conditions such that,
    (1) said first oligonucleotide primer hybridizes to said RNA first template,
    (2) said RNA-directed DNA polymerase uses said RNA first template to synthesize a DNA second template by extension of said first oligonucleotide primer and thereby forms an RNA-DNA hybrid intermediate,
    (3) said ribonuclease hydrolyzes RNA of said RNA-DNA hybrid intermediate,
    (4) said second oligonucleotide primer hybridizes to said DNA second template,
    (5) said DNA-directed DNA polymerase uses said second oligonucleotide primer and said DNA second template to synthesize a functional promoter recognized by said second RNA polymerase, and (6) said second RNA polymerase recognizes said functional promoter and transcribes said DNA second template, thereby providing copies of an RNA second template, and thereafter a cycle ensues wherein
(1) said second oligonucleotide primer hybridizes to said RNA second template,
(2) said RNA-directed DNA polymerase uses said RNA second template to synthesize a DNA third template by extension of said second oligonucleotide primer and thereby forms an RNA-DNA hybrid intermediate,
(3) said ribonuclease hydrolyzes RNA of said RNA-DNA hybrid intermediate,
(4) said first oligonucleotide primer hybridizes to said DNA third template,
(5) said DNA-directed DNA polymerase uses said first oligonucleotide primer as template to synthesize a functional promoter recognized by said second RNA polymerase by extension of said DNA third template, and
(6) said second RNA polymerase recognizes said functional promoter and transcribes said DNA third template, thereby providing copies of said RNA second template, and thereafter
(C) maintaining said conditions for a time sufficient to achieve a desired amplification of said specific nucleic acid sequence or of a sequence complementary to said specific nucleic acid sequence.

5. A process according to claim 4, wherein said first RNA polymerase is one selected from the group consisting of *Escherichia coli* RNA polymerase core and holoenzyme.

6. A process according to claim 4, wherein Step (A) further comprises providing deoxyribonucleoside triphosphates.

7. A process for the amplification of a specific nucleic acid sequence, comprising the steps of:
(A) providing reagents comprising at least,
(i) a DNA first template comprising the specific nucleic acid sequence,
(ii) a first RNA polymerase which is capable of non-specifically transcribing a DNA template independent of specific promoter sequences,
(iii) ribonucleoside triphosphates;
under conditions such that such first RNA polymerase uses said DNA first template to synthesize an RNA first template which comprises said specific nucleic acid sequence or a sequence complementary to said specific nucleic acid sequence,
(B) providing in one or more steps reagents comprising
(i) an inhibitor of said first RNA polymerase,
(ii) a first oligonucleotide primer, comprising a plus sequence of a promoter recognized by a second RNA polymerase,
(iii) a second oligonucleotide primer,
(iv) a second RNA polymerase which is a DNA-directed RNA polymerase that recognizes said promoter,
(v) an RNA-directed DNA polymerase,
(vi) a DNA-directed DNA polymerase,
(vii) a ribonuclease that hydrolyzes RNA of an RNA-DNA hybrid without hydrolyzing single or double-stranded RNA or DNA, and
(viii) ribonucleoside and deoxyribonucleotide triphosphates,
under conditions such that,
(1) said first oligonucleotide primer hybridizes to said RNA first template,
(2) said RNA-directed DNA polymerase uses said RNA first template to synthesize a DNA second template by extension of said first oligonucleotide primer and thereby forms an RNA-DNA hybrid intermediate,
(3) said ribonuclease hydrolyzes RNA of said RNA-DNA hybrid intermediate.
(4) said second oligonucleotide primer hybridizes to said DNA second template,
(5) said DNA-directed DNA polymerase uses said second oligonucleotide primer and said DNA second template to synthesize a functional promoter recognized by said second RNA polymerase, and
(6) said second RNA polymerase recognizes said functional promoter and transcribes said DNA second template, thereby providing copies of an RNA second template, and thereafter a cycle ensues wherein
(1) said second oligonucleotide primer hybridizes to said RNA second template,
(2) said RNA-directed DNA polymerase uses said RNA second template to synthesize a DNA third template by extension of said second oligonucleotide primer and thereby forms an RNA-DNA hybrid intermediate,
(3) said ribonuclease hydrolyzes RNA of said RNA-DNA hybrid intermediate,
(4) said first oligonucleotide primer hybridizes to said DNA third template,
(5) said DNA-directed DNA polymerase uses said first oligonucleotide primer as template to synthesize a functional promoter recognized by said second RNA polymerase by extension of said DNA third template, and
(6) said second RNA polymerase recognizes said functional promoter and transcribes said DNA third template, thereby providing copies of said RNA second template, and thereafter
(C) maintaining said conditions for a time sufficient to achieve a desired amplification of said specific nucleic acid sequence or of a sequence complementary to said specific nucleic acid sequence.

8. A process according to claim 7, wherein such inhibitor is rifampicin.

9. A process according to claim 4, wherein Step (A) is followed by heating said reagents and said RNA first template before Step (B).

10. A process according to claim 9, wherein said reaction medium is heated to about 65° C.

11. A process according to claim 4, further comprising providing an alkylated sulfoxide and a suitable carrier protein.

12. A process according to claim 11 wherein said alkylated sulfoxide is dimethylsulfoxide (DMSO) and wherein said carrier protein is bovine serum albumin (BSA).

13. A process according to claim 5, wherein said *Escherichia coli* RNA polymerase is provided at a concentration in the range of 1–3 units per 15 $\mu$l.

14. A process according to claim 7, wherein said inhibitor is provided at a concentration in the range of 10–100 $\mu$g per ml.

15. A process according to claim 4, wherein said first oligonucleotide primer further comprises a plus sequence of a transcription initiation site for said second RNA polymerase, said plus sequence of said transcription initiation site being operatively linked to said plus sequence of said promoter.

16. A process according to claim 15, wherein said second RNA polymerase is bacteriophage T7 RNA polymerase and wherein said plus sequence of a transcription initiation site and said plus sequence of said promoter together comprise the nucleotide sequence SEQ ID NO: 1

5'-AATTCTAATACGACTCACTATAGGGAGA-3'.

17. A process according to claim 4, wherein said process further comprises a step of monitoring said reaction medium for consumption of any of said first oligonucleotide primer, second oligonucleotide primer, and ribonucleoside and deoxyribonucleoside triphosphates or for accumulation of any product of said cycle.

18. A process according to claim 17, wherein said monitoring step comprises detecting the accumulation of said specific nucleic acid sequence or a sequence complementary to said sequence.

19. A process according to claim 18, wherein said monitoring step comprises detecting said sequence or the sequence complementary to said sequence using a nucleic acid probe.

20. A process according to claim 18, wherein said monitoring step comprises detecting said sequence or the sequence complementary to said sequence using restriction endonuclease and electrophoretic separation.

21. A process according to claim 17, wherein said monitoring step comprises monitoring the accumulation of said RNA second template.

22. A process according to claim 17, wherein said monitoring step comprises monitoring the accumulation of said DNA second template.

23. A process according to claim 17 which said monitoring step comprises monitoring DNA containing a functional promoter recognized by said second RNA polymerase.

24. A process according to claim 17, wherein said monitoring step comprises monitoring the accumulation of said RNA-DNA hybrid intermediate.

25. A process according to claim 17 wherein said monitoring step further comprises comparing consumption of any of said first oligonucleotide primer, second oligonucleotide primer, ribonucleoside and deoxyribonucleoside triphosphates or accumulation of any product of said cycle with a value representing consumption of said reagent or accumulation of said product in said reaction in the absence of said specific nucleic acid sequence and said sequence complementary thereto.

26. A process according to claim 4, further comprising conducting the process in a single reaction vessel.

27. A process according to claim 4, wherein said ribonuclease comprises calf thymus ribonuclease H.

28. A process according to claim 4, wherein said first oligonucleotide primer or said second oligonucleotide primer is bound reversibly to an immobilized support.

29. A process according to claim 4, wherein said DNA-directed RNA polymerase is a bacteriophage RNA polymerase.

30. A process according to claim 29, wherein said DNA-directed RNA polymerase is bacteriophage T7 RNA polymerase.

31. A process according to claim 29, wherein said DNA-directed RNA polymerase is bacteriophage T3 polymerase.

32. A process according to claim 29, wherein said DNA-directed RNA polymerase is bacteriophage ΦII polymerase.

33. A process according to claim 29, wherein said DNA-directed RNA polymerase is Salmonella bacteriophage sp6 polymerase.

34. A process according to claim 29, wherein said DNA-directed RNA polymerase is Pseudomonas bacteriophage gh-1 polymerase.

35. A process according to claim 4, wherein said RNA-directed DNA polymerase is a retrovirus reverse transcriptase.

36. A process according to claim 35, wherein said retrovirus reverse transcriptase is avian myeloblastosis virus polymerase.

37. A process according to claim 35, wherein said retrovirus reverse transcriptase is a Moloney murine leukemia virus polymerase.

38. A process according to claim 4, wherein said ribonuclease is *Escherichia coli* ribonuclease H.

39. A process according to claim 4, wherein said DNA-directed DNA polymerase lacks exonuclease activity.

40. A process according to claim 4, wherein all DNA polymerases in said reaction medium lack DNA exonuclease and DNA endonuclease activity.

41. A process according to claim 4, wherein said DNA-directed DNA polymerase is avian myeloblastosis virus polymerase.

42. A process according to claim 4, wherein said DNA-directed DNA polymerase is DNA polymerase a or DNA polymerase β.

43. A process according to claim 4, wherein said DNA-directed DNA polymerase is calf thymus DNA polymerase.

44. A process according to claim 4, wherein Step (C) comprises maintaining said conditions for a time between 30 minutes and 4 hours.

45. A process according to claim 4, further comprising the steps of ligating a DNA product of said cycle into a cloning vector and then cloning said DNA product.

46. A process according to claim 4, further comprising the step of expressing a product encoded by said DNA second template or said DNA third template in an expression system.

47. A kit for amplifying nucleic acid sequences, comprising one or more receptacles containing
(a) a DNA-directed RNA polymerase capable of non-specifically transcribing a DNA template independent of specific promoter sequences,
(b) ribonucleoside triphosphates,
(c) deoxyribonucleotide triphosphates,
(d) a first oligonucleotide primer comprising a plus sequence of a promoter recognized by a second RNA polymerase,
(e) a second oligonucleotide primer,
(f) a second RNA polymerase which is a DNA-directed RNA polymerase that recognizes said promoter,
(g) an RNA-directed DNA polymerase,
(h) a DNA-directed DNA polymerase,
(i) a ribonuclease that hydrolyzes RNA of an RNA-DNA hybrid without hydrolyzing single- or double-stranded RNA or DNA, and
(j) an inhibitor of the DNA-directed RNA polymerase capable of non-specifically transcribing a DNA template independent of specific promoter sequences.

48. A kit as set forth in claim 47, wherein said first RNA polymerase is *Escherichia coli* RNA polymerase.

49. A kit as set forth in claim 48 wherein the inhibitor is an inhibitor of *Escherichia coli* RNA polymerase.

50. A kit as set forth in claim 49, wherein the inhibitor is rifampicin.

51. A kit as set forth in claim 47, further comprising a receptacle containing an alkyated sulfoxide and a receptacle containing a suitable carrier protein.

52. A kit for amplifying nucleic acid sequences, comprising one or more receptacles containing
 (a) a DNA-directed RNA polymerase capable of non-specifically transcribing a DNA template independent of specific promoter sequences,
 (b) a first oligonucleotide primer comprising a plus sequence of a promoter recognized by a second RNA polymerase,
 (c) a second oligonucleotide primer,
 (d) a second RNA polymerase that recognizes said promoter,
 (e) a DNA polymerase, and
 (f) an inhibitor of the DNA-directed RNA polymerase capable of non-specifically transcribing a DNA term independent of specific promoter sequences.

53. A kit of claim 48, further comprising a receptacle containing a ribonuclease that hydrolyzes the RNA of an RNA-DNA hybrid without hydrolyzing single- or double-stranded RNA or DNA.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

AATTCTAATA CGACTCACTA TAGGGAGA          28